United States Patent [19]

Mateescu et al.

[11] Patent Number: 5,603,956
[45] Date of Patent: Feb. 18, 1997

[54] CROSS-LINKED ENZYMATICALLY CONTROLLED DRUG RELEASE

[75] Inventors: Mircea A. Mateescu, Verdun; Yves Dumoulin, Ste-Julie; Louis Cartilier, Beaconsfield; Vincent Lenaerts, Argenteuil, all of Canada

[73] Assignee: Labopharm Inc., Ste-Therese, Canada

[21] Appl. No.: 261,228

[22] Filed: Jun. 16, 1994

Related U.S. Application Data

[63] Continuation of Ser. No. 919,762, Jul. 24, 1992, abandoned, which is a continuation-in-part of Ser. No. 787,721, Oct. 31, 1991, abandoned, which is a continuation of Ser. No. 618,650, Nov. 27, 1990, abandoned.

[51] Int. Cl.$^6$ .................................................. A61K 47/36
[52] U.S. Cl. ........................................ 424/488; 424/94.1
[58] Field of Search .................................. 424/488, 94.1

[56] References Cited

U.S. PATENT DOCUMENTS

| | | | |
|---|---|---|---|
| 2,987,445 | 6/1961 | Levesque | 424/94 X |
| 3,087,860 | 4/1963 | Endicott | 424/94 X |
| 3,181,998 | 5/1965 | Kanig | 167/82 |
| 3,493,652 | 2/1970 | Hartman | 424/94 |
| 3,622,677 | 11/1971 | Short | 424/94 X |
| 4,088,798 | 5/1978 | Michaelis | 424/94 X |
| 4,124,705 | 11/1978 | Rothman | 424/94 |
| 4,230,687 | 10/1980 | Sair | 424/94 X |
| 4,344,968 | 8/1982 | Aoda et al. | 424/94 X |
| 4,369,308 | 1/1985 | Trubiano | 424/94 X |
| 4,713,249 | 12/1987 | Schroder | 424/94 X |
| 4,755,397 | 7/1988 | Eden et al. | 424/94 X |
| 4,761,289 | 8/1988 | Shalati et al. | 424/94 X |
| 4,812,445 | 3/1989 | Eden et al. | 424/94 X |
| 4,814,182 | 3/1989 | Graham et al. | 424/94 X |
| 4,933,185 | 6/1990 | Wheatley et al. | 424/461 |
| 4,952,402 | 8/1990 | Sparks et al. | 424/94 X |
| 5,108,758 | 4/1992 | Allwood et al. | 424/468 |

FOREIGN PATENT DOCUMENTS

| | | |
|---|---|---|
| 2041774 | 5/1992 | Canada. |
| WOA8900045 | 1/1989 | WIPO. |

OTHER PUBLICATIONS

J. of Controlled Release vol. 15, No. 1, Feb. 1991 Lenaerts et al pp. 39–46.
V. Lenaerts et al., "Controlled Release of Theophylline from Cross–linked Anylose Tablets" *Journal of Controlled Release* 15(1): 39–46 (1991).
Canada (Abstract), Derwent Publications, Week 9233, May 28, 1992, CA A2 041 774.
Pharm. ACTA Helv. 56, Nr. 4–5 (1981).
Pharm. ACTA helv. 55, Nr. 6 (1980).
Journal of Polymer Science: Polymer Physics Edition, vol. 21, 983–997 (1983).
Analytical Letters, 14 (B17 & B18), 1501–1514 (1981).

*Primary Examiner*—Peter F. Kulkosky
*Attorney, Agent, or Firm*—Foley & Lardner

[57] ABSTRACT

The present application is concerned with a solid slow release pharmaceutical dosage unit. More specifically, the invention is directed to a tablet form prepared by direct compression of cross-linked amylose (CLA) having a definite cross-linking degree, α-amylase and a pharmaceutical agent. The presence of the cross-linked amylose allows a sustained release of the drug, while the α-amylase permits the modulation of the release time. In other words, the release time of the drug is function of the amount of α-amylase in the tablet. The amount of α-amylase is defined in terms of Enzyme Units.

10 Claims, 5 Drawing Sheets

CROSS-LINKED ENZYMATICALLY CONTROLLED DRUG RELEASE

CROSS-REFERENCE TO RELATED APPLICATION

This application is a continuation of application Ser. No. 07/919,762, filed Jul. 24, 1992, abandoned, which is a continuation-in-part of U.S. patent application Ser. No. 07/787,721 filed Oct. 31, 1991, abandoned, which is a continuation of U.S. patent application Ser. No. 07/618,650, filed Nov. 27, 1990, abandoned.

FIELD OF THE INVENTION

The present invention is concerned with a solid slow release pharmaceutical dosage unit, incorporating cross-linked amylose (CLA) and associated α-amylase as slow release matrix. The drug release is controlled enzymatically by two different sequential molecular mechanisms.

BACKGROUND OF THE INVENTION

The interest for monolithic devices for the controlled release of drugs is continuously growing, and much effort has been done for the development of novel pharmaceutical dosage forms ensuring more constant release rate of liberation over extended periods of time.

Various polymers, such as vinylic polymers, polyethylene, silicone, ethylcellulose, acyl-substituted cellulose, poly(hydroxyethylmethacrylate)-PHEMA, acrylic copolymers and the like, have been proposed for use as matrices for drug controlled release, (see for example U.S. Pat. No. 3,087,860, U.S. Pat. No. 2,987,445, U.S. Pat. No. 4,761,289 and Pharm. Acta Helv., 1980, 55, 174–182, Salomon et al.). Despite the multitude of these polymeric matrices that have been developed (hydrogels, hydrophillic, hydrophobic and the like), no ideal matrix conferring a sustained drug release at a constant rate is known. In this context, many physical and chemical systems have been suggested, most of them based on diffusion-controlled, swelling-controlled or chemically-controlled (external bioerosion) drug release.

The diffusion controlled systems, which require hydrophillic polymers such as hydroxyethylcellulose, sodium-carboxymethylcellulose and the like, allow a sustained release of drugs, but do not permit a rigorous control since the release rate is not constant.

The swelling-controlled systems are based on glassy homogeneous polymeric matrices free of internal channels, into which the water front penetrates at a constant rate. Behind this front, the polymer is in a rubbery state. If the diffusion coefficient of the drug is significantly higher in the rubbery state than in the glassy state of the polymer, a zero order release can be obtained, but only for a limited degree of release, usually around 60% from the total amount of loaded drug, and this only for the case of relatively low initial drug concentration (see N. Peppas and N. Franson, J. Polym. Sci., 21, 983–997, 1983. Another mechanism allows a slow drug release mediated by the tablet external bioerosion during its gastroenteric residence (E. Doelker and P.Buri, Pharm. Acta Helv., 56, 111–117, 1981). This system is mainly based on starch or lipidic matrices, and the rate of drug release is related to the complex composition of the gastric fluids (including its enzymatic set) and is therefore susceptible to variations from one individual to another.

Although these mechanisms allow interesting release kinetics, the release times and the linearity of the dissolution curves, are still to be improved.

Cross-linked amylose (CLA), a semisynthetic material obtained by the cross-linking of amylose with a cross-linking agent such as epichlorohydrin or 2,3-dibromopropanol, has recently been introduced as a matrix for drug controlled slow release, wherein the drug dissolution rate is controlled by a mechanism based on hydrogen associations established following the compression, between amylose chains (see U.S. Ser. No. 787,721 filed Oct. 31, 1991). Such CLA matrix provides substantially linear release kinetics.

However, the release times of certain drugs, mainly the ones with a limited aqueous solubility or presenting some affinity interactions with the CLA matrix, can sometimes be higher than the usual release time observed for the majority of pharmaceutical products, which is about 15–24 hours. Release times exceeding 24 hours are generally undesirable, except for rare occasions. Furthermore, there are several drugs (cardiovascular, anaesthetics, sedatives, antihistaminics, etc.) for which the optimal release time is of 6–12 h.

It would therefore be highly desirable to obtain a slow release pharmaceutical dosage unit which would permit a controlled slow release of the drug present therein. Such pharmaceutical dosage unit would further allow the control of the time of release depending on the optimal time required for a given pharmaceutical product.

SUMMARY OF THE INVENTION

In accordance with the present invention, there is provided a solid slow release pharmaceutical dosage unit made up of an admixture of 1) a therapeutic dosage of a pharmaceutical product; 2) a cross-linked polymer of amylose with a cross-linking agent, wherein the cross-linking has been carried out with from about 1 to about 20 grams of cross-linking agent per 100 grams of amylose; and 3) an enzyme for modulating the release of the pharmaceutical product. Preferably the pharmaceutical dosage unit comprises at least 40% by weight of cross-linked amylose (CLA), and no more than 60% by weight of a pharmaceutical product. The amount of α-amylase present in the tablet is determined by its Enzyme Unit (EU) activity. Typically, an activity of 100 EU or less per tablet is sufficient. However, depending on the release time desired for a given pharmaceutical product, the enzyme activity can be modified at will in the tablet.

The cross-linked amylose used in the course of the present invention is obtained by cross-linking amylose with a suitable cross-linking agent, such as epichlorohydrin, 2,3-dibromopropanol and the like. Preferably, from 1 to 20 g of cross-linking agent are used per 100 g of amylose, corresponding to a cross-linking degree of 1 to 20, or CLA-1 to CLA-20 respectively, CLA-6 being the most preferred cross-linking degree.

In an aspect of the present invention, the particles of the cross-linked polymer of amylose have a size that varies generally between about 0.5 and about 5 microns. These particles form agglomerates of approximately 25–700 microns, as observed by Scanning Electron Microscopy (SEM).

IN THE DRAWINGS

DETAILED DESCRIPTION OF THE INVENTION

Figure 1:
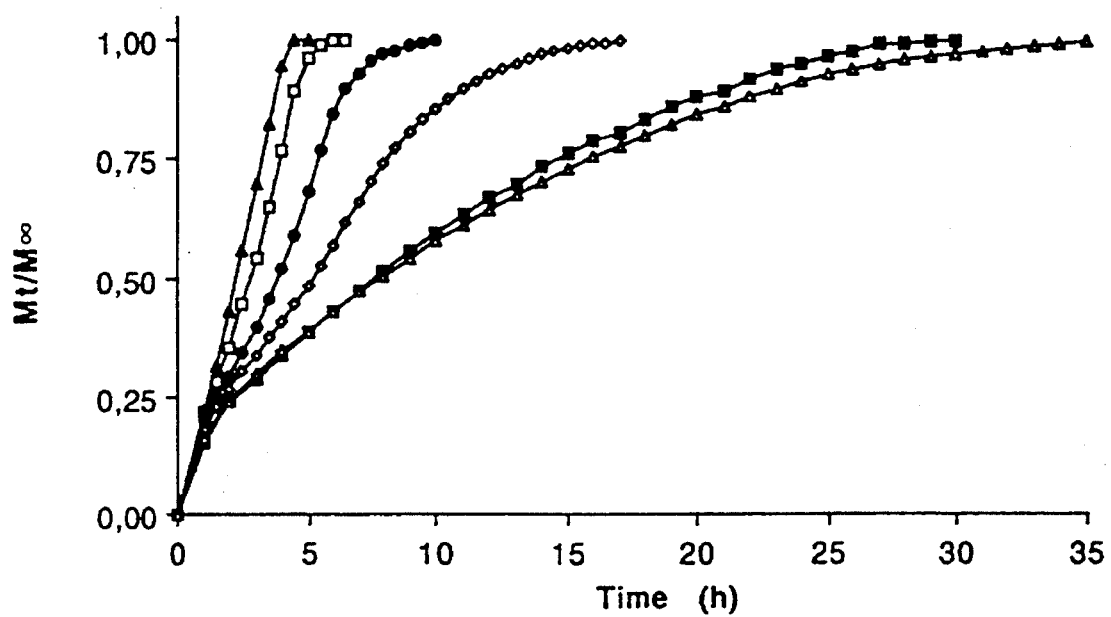
FIG. 1 illustrates the release profiles of theophylline in a tablet prepared in accordance with the present invention.

The mechanism involved in the dosage unit of the present invention consists in that α-amylase is able to specifically recognize the CLA polymer as a semisynthetic substrate, and to catalyse the hydrolysis of its α-1,4 glucosidic bonds. The rate of the enzymatic hydrolysis is limited by the rate of water front penetration, which is itself controlled by the interchain hydrogen associations. Therefore, the amylose chains are slowly and partially nicked, but with the preservation of the three-dimensional structure over a long period, since the polymer is articulated by multiple amylose interchain bridges introduced by the cross-linking agent, and by interchain hydrogen associations created during the compression of the tablet. The release of the drug is therefore easily modulated by the α-amylase enzyme kinetics, which are controlled by the above mechanism.

The solid slow release pharmaceutical dosage unit of the present invention can be obtained by the direct compression of an admixture of the drug in the required dosage, with an amount of α-amylase corresponding to a definite number of enzyme units, and with the CLA polymer.

The amount of α-amylase in the CLA matrix depends on the required release time for a given drug under optimal release conditions. The present invention allows controlled release dosage units forms of various types of drugs. It is of importance however to note that the pharmaceutical product present in the solid slow release dosage unit of the present invention must not inhibit the activity of the α-amylase, since it would then destroy the beneficial effect of same. For example, if an acidic drug is associated with the dosage unit of the present invention, it is preferred to incorporate a buffer in the tablet in order to avoid such undesirable interactions between the drug and the enzyme.

Amylose is a natural substance obtained from starch, a binary compound constituted by the amylose, based on non-ramified polyglucose chains, wherein the repetitive glucose units are linked by α-1,4-glucosidic bonds, and by the amylopectin branched polyglucose polymer with an important frequency of branching points based on α-1,6-glucosidic bonds.

The α-amylase (EC 3.2.1.1) is the enzyme catalysing the specific hydrolysis of internal α-1,4-glucosidic bonds in polyglucose polymers such as starch, amylose and some of their derivatives.

Cross-linked amylose and the α-amylase

Cross-linked Amylose (CLA) is a semisynthetic material exhibiting a three-dimensional structure, wherein the polyglucose chains are linked by transversal bridges introduced by the cross-linking reaction. In order to obtain cross-linked amylose, the amylose is swollen in alkaline medium in a planetary mixer, with homogenization, and then the required amount of cross-linking agent is added, with moderate heating (40°–70° C.), continuing the reaction for a period of up to 1 hour. The type and the amount of cross-linking agent, as well as the reaction time, can be varied. The resulting CLA is then dehydrated, dried and sieved, with retention of the particles having a size ranging approximately from 75–297 μm.

It is well known that α-amylase is able to recognize cross-linked amylose gel as a modified substrate, by affinity interactions (Mateescu et al, Anal. Lett., 14, 1501–1511, 1981). The present invention now demonstrates that α-amylase is able to hydrolyse the α-1,4-glucosidic bonds of CLA in tablet forms, which allow an enzymatic controlled drug release (ECDR) system.

Preparation of tablets

As shown in U.S. Ser. No. 787,721, filed Oct. 31, 1991, various drugs can be directly compressed with CLA matrices, leading to sustained release forms wherein release times and kinetics are controlled by interchain hydrogen associations. The present application presents a novel controlled release system, wherein the release kinetics are highly correlated with the hydration and with the enzymatic hydrolysis of the CLA matrix. To realize such Enzyme Controlled Drug Release (ECDR) mechanism, α-amylase is incorporated in the tablet. Tablets of approximately 500 mg were prepared, containing amounts of α-amylase of up to 20 mg, corresponding to enzyme activities of up to 100 EU (Enzyme Units) per tablet. One EU is typically defined as the amount of enzyme necessary to catalyse the liberation of one μmole of maltose per minute. Different drugs, for instance Theophylline, Aspirin, Acetaminophen, Acetanilide and Carnitine were selected for tests purposes. It will become obvious for any man skilled in the art that the present invention is not to be limited to these particular pharmaceutical products, but can also be applied to any drug with the restriction that the drug does not inhibit the activity of the α-amylase.

Tablets of 13 mm diameter and 2.7–4.5 mm thickness were prepared by direct compression in a hydraulic press at more than 0.5 T/cm$^2$; unexpectedly and differently from the literature data, the release kinetics are not influenced by the compression strength of the tablet for the cross-linking range allowing the matrix stabilization by hydrogen associations.

The cross-linking degree, expressed as the amount (in grams) of cross-linking agent used per 100 g of amylose, is a critical parameter for the tablet's stabilization of hydrogen associations. Only low cross-linking degrees, that is from 1 to 20, allow hydrogen bonding, because the length of the interchain glyceric bridges produced by the cross-linking is about 8.7 Å, and if they are not sufficiently distant from one another, hydrogen bonding (5.7 Å) does not occur. The preferred amylose cross-linking degree is 6, but it must be kept in mind that other cross-linking degrees can be used, provided that they allow stabilization of the tablet by hydrogen associations, which control the hydration and consequently the hydrolyric enzyme activity. The slow water penetration reduces the rate of enzymatic hydrolysis to only a limited number of α-1,4-glucosidic bonds. Thus, the advancement of the partial nicking of the structure is limited to a few points only and therefore the drug release is well controlled by the two mechanisms implied: the hydrogen association and the ECDR.

Studies of in vitro drug release from tablets

Tablets were placed individually in 1 l buffer solutions (phosphate, TRIS-HCl) at 37° C. in a Hanson dissolution apparatus (rotating paddle 100 rpm) and the release data recorded with a Beckman DU-65 equipped with the dissolution data system.

Cross-linked amylose and α-amylase are extremely advantageous species for preparing the enzymatically controlled drug release dosage unit of the present invention. Cross-linked amylose is easy to manufacture, and the resulting tablets are prepared simply by direct compression. Furthermore, the dosage unit of the present invention is remarkably versatile, since it allows a large choice of drug release times, which are easily regulated by the number of Enzyme Units incorporated in the tablet. The system affords the possibility to maintain the controlled release even at relatively high drug concentration, that is up to 60%. At the same time, the CLA matrix exhibits a high biocompatibility and an excellent in vivo biodegradability.

The following examples are provided to illustrate the invention rather than limit its scope. Other variations within the scope of the present invention will be easily appreciated by the skilled workman.

EXAMPLE 1

Cross-linked amylose synthesis 1 kg of amylose and 6 l of sodium hydroxide 1N were homogenized for 20 minutes in a Hobart™ planetary mixer tank A-200T at 55° C. Subsequently, 60 g (50.8 ml) of epichlorohydrin were added. After 20 minutes of homogenization, the mixture was neutralized with acetic acid, and the cross-linked amylose was filtered and washed with a solution of water/acetone (15:85) in a first step and then with water/acetone (60:40). The CLA was dried with acetone and then allowed to stand for 3 hours. The dry polymer was sieved (mesh openings of 75–297 μm) and stored at room temperature. The cross-linking degree of this polymer being 6, it will be further referred to as CLA-6.

Other CLA polymers with cross-linking degrees of 1, 4, 12 and 20 were synthesized in similar conditions, that is, 1, 4, 12 and 20 g epichlorohydrin/100 g of amylose.

EXAMPLE 2

Tablets containing theophylline as the active agent

Powders of theophylline, α-amylase and CLA-6 as obtained in Example 1 were mixed during three minutes, in a Turbula™ mixer in such proportion as to obtain CLA-6 tablets containing 100 mg of theophylline each, and amounts of α-amylase in the range 0–5 mg, the remainder being CLA-6. The tablets (thickness=2.7 mm; diameter=13 mm and weight=500 mg) were obtained by direct compression at more than 2.4 T/cm$^2$, in a Carver™ hydraulic press. The enzyme used is pancreatic α-amylase, manufactured and sold by Sigma Chem. Co., St-Louis, Mo., and possesses a specific activity of 5 EU/mg protein. The activity of the enzyme was verified prior to the preparation of the tablet containing same. The release profile of these tablets is illustrated in FIG. 1.

EXAMPLE 3

Tablets containing 4-acetaminophenol (Acetaminophen) as the active agent

Figure 2:
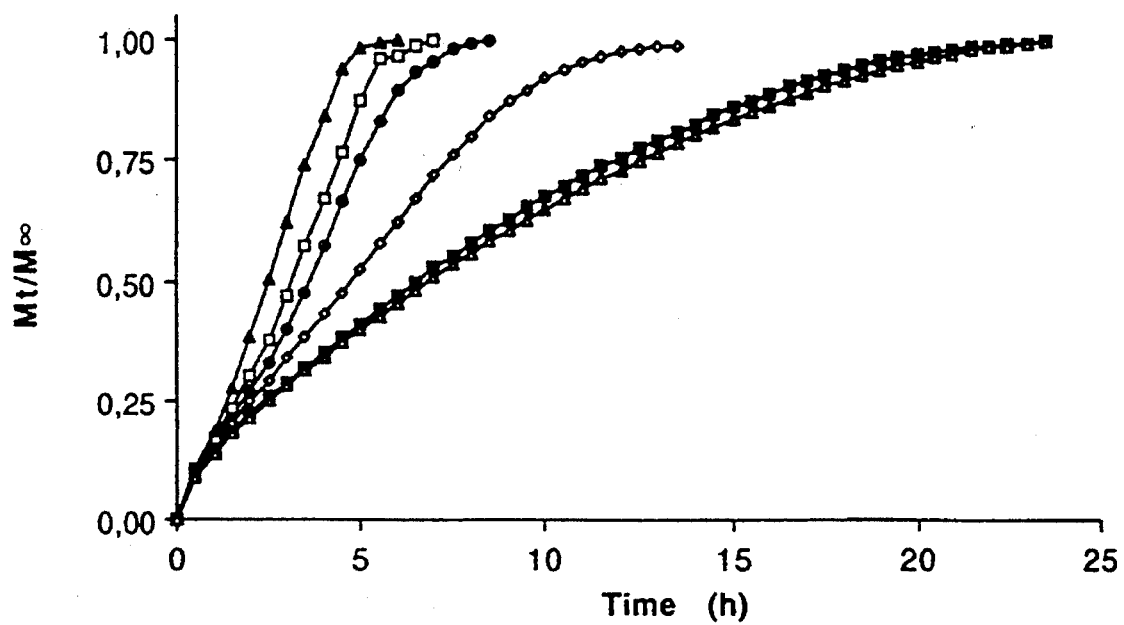
FIG. 2 illustrates the release profiles of 4-acetaminophenol (acetaminophen) in a tablet prepared in accordance with the present invention.

Tablets of 500 mg, each made of CLA-6 containing 100 mg of 4-acetaminophenol and 0, 1, 2, 3 or 5 mg of α-amylase respectively, were prepared in the same manner as in Example 2. The release profile of these tablets is illustrated in FIG. 2.

EXAMPLE 4

Tablets containing acetanilide as the active agent

Figure 3:
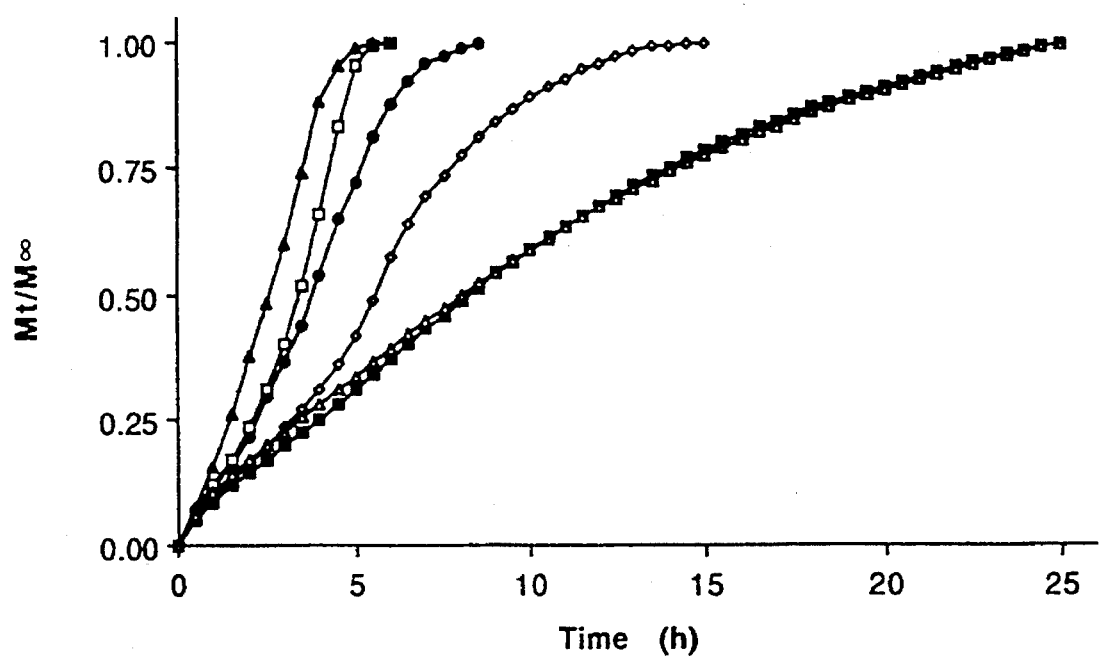
FIG. 3 illustrates the release profiles of acetanilide in a tablet prepared in accordance with the present invention.

Tablets of 500 mg, each made of CLA-6 containing 100 mg of acetanilide and 0, 1, 2, 3 or 5 mg of α-amylase respectively, were prepared in the same manner as in Example 2. The release profile of these tablets is illustrated in FIG. 3.

EXAMPLE 5

Drug release monitoring and in vitro drug release results

Each tablet is placed in 1 l of NaHPO$_4$/Na$_2$HPO$_4$ buffer (100 mM, pH 7.0 at 37° C.). In all the examples, the drug release is monitored in a USP dissolution apparatus equipped with a mechanical stirrer (100 rpm). The release is recorded spectrophotometrically at an appropriate wavelength (theophylline $\lambda$=290 nm, acetaminophen $\lambda$=280 nm and acetanilide $\lambda$=270 nm) with a Beckman DU-65 spectrophotometer.

In all the cases, it is clear that it is possible to modulate the release time of the drug by varying the enzymatic activity (number of Enzyme Units) of the α-amylase associated with the matrix, i.e. the amount of α-amylase in the tablet. For the pharmaceutical products chosen to illustrate the advantages of the present invention, in the absence of α-amylase the release times were of 30 hours for the theophylline (FIG. 1), 25 hours for the acetaminophen (FIG. 2) and 23 hours for the acetanilide (FIG. 3).

Figure 4:
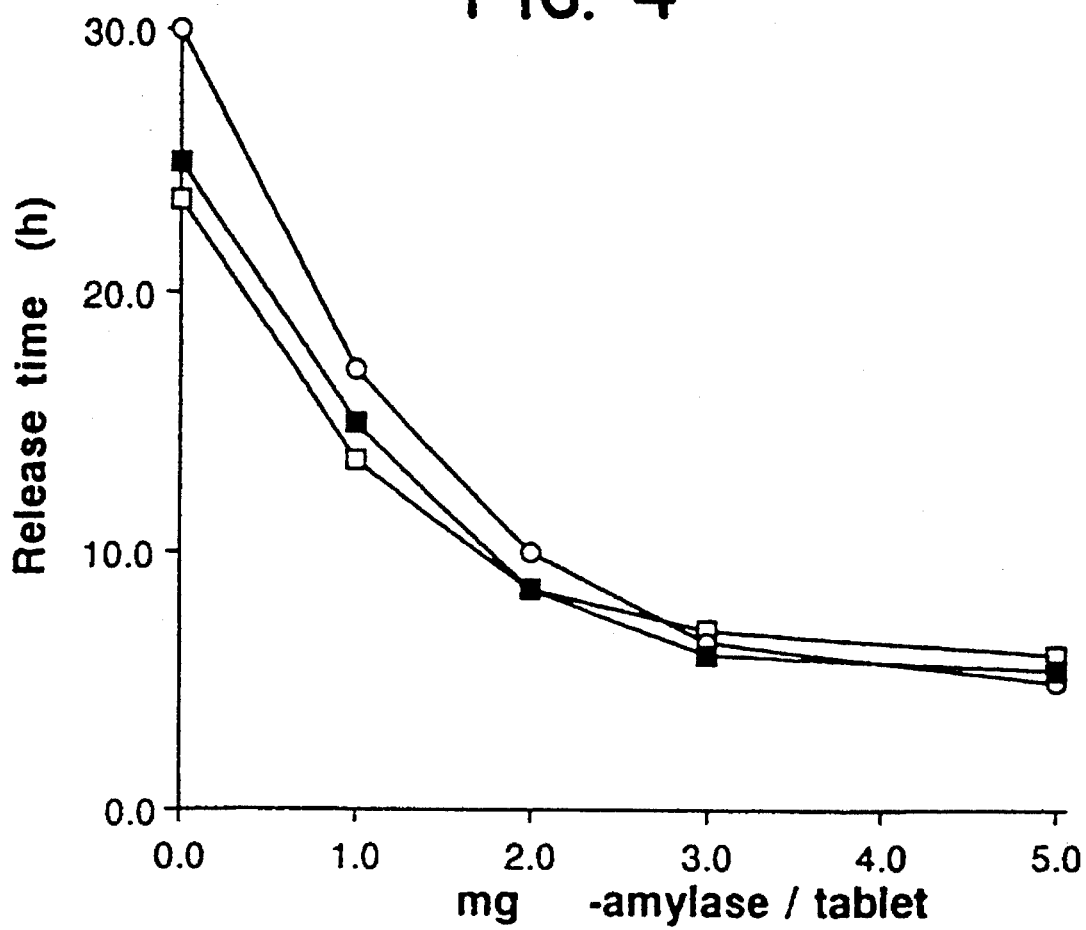
FIG. 4 illustrates the total release time of several drug depending on the contents of α-amylase in the tablet.

In the presence of increased amounts of α-amylase (0, 1, 2, 3 and 5 mg/tablet) the release times decrease regularly (FIG. 4) following a dose to logarithmic feature.

The release fractions ($M_t/M_\infty$) versus the α-amylase curves indicate the same dependency, irrespective to the nature of the drug (provided obviously that no interactions drug—α-amylase occur). FIGS. 1–4 illustrate that for a given pharmaceutical drug, the release time can easily be modulated with enough precision, by means of varying the content of α-amylase in the tablet. Control experiments with tablets prepared in accordance with Examples 2 to 4 without α-amylase, but containing 15 mg of Bovine Serum Albumin (BSA) indicated a very similar dissolution profiles as for the corresponding tablets without BSA and without α-amylase (FIGS. 1–3). In other words, BSA has no effect on the release profile of the active agents. Accordingly, these results show that the beneficial effect of α-amylase is not due to a modification of the tablet content, which means that the modulation of the release time is exclusively due to the α-amylase kinetics.

The new Enzyme Controlled Drug Release (ECDR) herein presented based on the associated α-amylase with the CLA matrix within the tablet, is different from the External Bioerosion approach as release controlling system. The bioerosion mechanisms are based on the action of the external constituents (enzymes, ions, etc.) of the dissolution medium (e.g. gastric fluids) to generate gradual erosion of the tablets starting with the marginal layers. It is well known that these systems imply serious individual variations. The ECDR mechanism is based on internal enzymatic attack, initiated and conditioned by the water front penetration. The hydration and the CLA matrix swelling are controlled by the interchain hydrogen associations created by the compression of the cross-linked amylose during the preparation of the tablets.

Therefore, the drug release mechanism proposed in the present application is the result of two separate actions closely related to one another:

1) the hydrogen association, which control a slow equilibrium process of amylose-amylose hydrogen links dissociations and amylose-water association, generating the amylose hydroxyl groups hydration and the matrix swelling; and 2) Enzyme Controlled Drug Release: once low amounts of water penetrate the matrix, the α-amylase is gradually activated, thus controlling a limited enzymatic hydrolysis of α-1,4-glucosidic bonds of the CLA matrix.

The chains are therefore partially nicked, since the points of lysis are statistically distanced, in function of the α-amylase activity and the water penetration. The lysis doesn't lead necessarily to a massive breakdown of the matrix structure and to the excision of the oligosaccharidic fragments since the cross-linked amylose chains are articulated in a three-dimensional structure by multipoints cross-linking (several glucose units of vicinal amylose chains are simultaneously implied in the cross-linking by the cross-linking agent reaction).

For instance, even when submitted to a partial lysis, cross-linked amylose can be viewed as a global three-dimensional structure where at the level of nicking points, oligoglucidic fragments are still retained as "hinge joints" by the matrix, becoming mobile and hydrated, allowing the release of the drug. Enzymatic dosages, infrared and X-ray data as well as calorimetric studies support these considerations. As far as the α-amylase mechanism of action is concerned, despite the fact that the cross-linked amylose is in a solid phase and chemically modified, the general enzyme kinetic rules apply, with the mention that the enzyme is not saturated with water, which is the case for general hydrolytic enzyme reactions in aqueous medium, but saturated with the solid substrate, namely cross-linked amylose. With the gradual penetration of the water acting as the second substrate, the enzyme initiates its catalytic activity. The velocity of the enzymatic hydrolysis increases with the gradual water front penetration, according to the Michaelis-Menten kinetic theory, explaining the slight increase of the slope of the release curves (FIGS. 1–3) after a few hours of immersion into the dissolution medium. Although the general aspect of the release curves is close to linear, this slightly sigmoidal feature clearly indicates that most probably there are two mechanisms implied in the enzymatically controlled drug release from the cross-linked amylose matrix.

Figure 5:
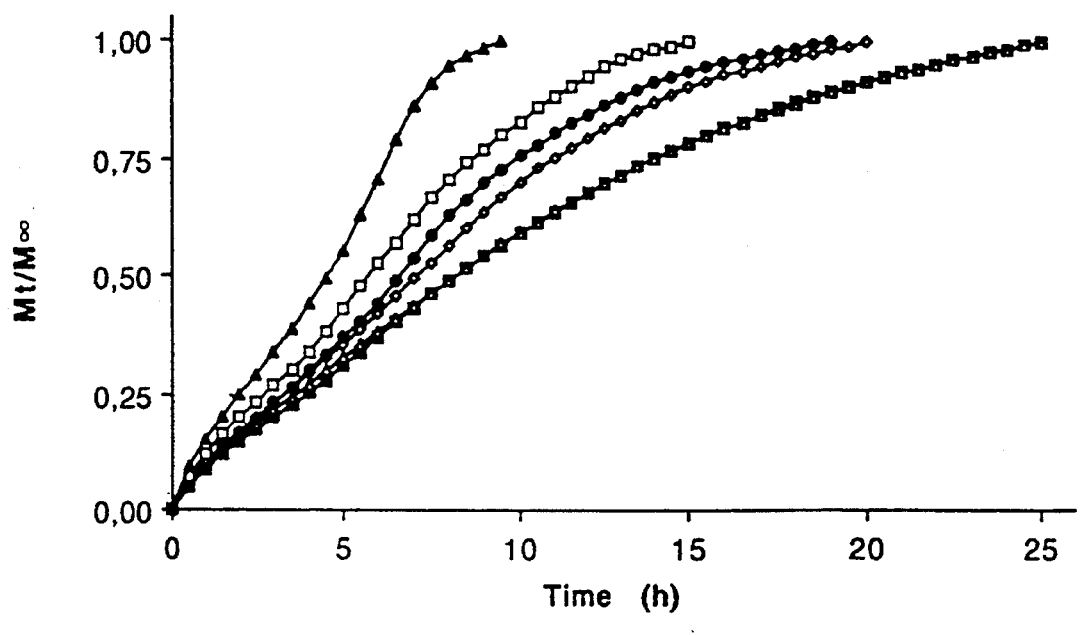
FIG. 5 illustrates the influence of the activity of α-amylase in the dissolution media on the release profiles of acetanilide.

The association of the α-amylase with a CLA matrix creates conditions of α-amylase substrate saturation (for example 395–400 mg CLA-6 compacted with 5 mg or less of α-amylase into a tablet having a dry volume of $0.4cm^3$). Therefore, unique kinetic conditions are accomplished for an effective control of the drug release, such as to obtain a required release time. These kinetic parameters also substantially differentiate our approach from the external bioerosion. These differences are illustrated by a comparative experiment, the results of which are presented in FIG. 5, where acetanilide (an antipyretic) was chosen as a tracer. The release curves were recorded for tablets of 500 mg containing 400 mg of CLA-6 and 100 mg of acetanilide, in the dissolution medium (sodium phosphate buffer, pH 7) containing increasing α-amylase concentrations (0–1200 mg/l, corresponding to 0–6000 EU/l), simulating thus the external bioerosion. The dissolution curves indicated that similar effects on the release time as for the α-amylase associated to the matrix (1 mg α-amylase/tablet in 1 l dissolution medium) can be obtained only with an α-amylase activity of at least 600 times higher (600 mg α-amylase in 1 l dissolution medium, corresponding to 3000 EU/l). This difference clearly indicates that the kinetic mechanisms are substantially different.

It is well known that, in agreement with the enzyme kinetic rules, a linear dependency of the reaction rate can be accomplished only in conditions of enzyme saturation with substrate. Consequently, ensuring the enzyme saturation, the procedure adopted in the present application allows the modulation of the release time, via the α-amylase activity within the tablet, in function of therapeutic requirements. The external bioerosion system is unable, in similar conditions with the cross-linked amylose tablets, to ensure the enzyme saturation with the substrate and consequently, unable to allow the modulation of the release time. Furthermore, it is worth mentioning that for normal subjects, the level of pancreatic α-amylase is lower than 120 EU/l. In other words, at this physiologic level, there are no significant differences induced by the α-amylase on the drug release kinetics. Therefore, the control of the release of the drug is entirely due to the α-amylase associated with the cross-linked amylose matrix within the tablet.

What is claimed is:

1. A solid controlled release pharmaceutical dosage unit in the form of a compressed mixture consisting essentially of:

up to 60% by weight of a therapeutically effective product;

at least 40% by weight of amylose cross-linked with a cross-linking agent selected from the group consisting of epichlorohydrin and 2,3-dibromopropanol, wherein said cross-linked amylose is prepared by cross-linking amylose with from 1 to 20 grams of said cross-linking agent per 100 grams of amylose, and wherein said cross-linking provides sustained release of said therapeutically effective product; and an enzyme for modulating the release of the pharmaceutical product, said enzyme being an α-amylase present in an amount corresponding to an enzyme activity of 100 EU or less per dosage unit.

2. The pharmaceutical dosage unit of claim 1, wherein the enzyme is present in an amount corresponding to an enzyme activity of 100 EU per tablet or less.

3. The pharmaceutical dosage unit of claim 1, wherein the cross-linking agent is epichlorohydrin.

4. A solid controlled release pharmaceutical dosage unit according to claim 1, wherein the release time of the solid controlled release pharmaceutical dosage unit containing the α-amylase is about 15 to 24 hours.

5. A solid controlled release pharmaceutical dosage unit according to claim 1, wherein the release time of the solid controlled release pharmaceutical dosage unit containing the α-amylase is 6 to 12 hours.

6. A solid controlled release pharmaceutical dosage unit according to claim 3, wherein the release time of the solid controlled release pharmaceutical dosage unit containing the α-amylase is about 15 to 24 hours.

7. A solid controlled release pharmaceutical dosage unit according to claim 3, wherein the release time of the solid controlled release pharmaceutical dosage unit containing the α-amylase is 6 to 12 hours.

8. The pharmaceutical dosage unit of claim 3, wherein the cross-linking is carried out with about 6 grams of epichlorohydrin per 100 grams of amylose.

9. The pharmaceutical dosage unit of claim 1, wherein said compressed mixture is in the form of a tablet.

10. The pharmaceutical dosage unit of claim 9, wherein said tablet is prepared by direct compression in a press at more than 0.5 T/cm$^2$.

* * * * *